(12) United States Patent
Yamagata et al.

(10) Patent No.: US 8,594,413 B2
(45) Date of Patent: Nov. 26, 2013

(54) IMAGE PROCESSING APPARATUS

(75) Inventors: Yoshifumi Yamagata, Otawara (JP);
Tomohiro Kawasaki, Otawara (JP);
Satoshi Wakai, Nasushiobara (JP)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 120 days.

(21) Appl. No.: 13/343,016

(22) Filed: Jan. 4, 2012

(65) Prior Publication Data

US 2013/0108141 A1    May 2, 2013

Related U.S. Application Data

(60) Provisional application No. PCT/JP2011/075330, filed on Nov. 2, 2011.

(51) Int. Cl.
*G06K 9/00* (2006.01)
*A61B 5/02* (2006.01)

(52) U.S. Cl.
USPC .......................... 382/134; 382/274; 600/483

(58) Field of Classification Search
USPC ......... 382/100, 103, 106–107, 128–133, 154, 382/168, 173, 181, 199, 232, 254, 274, 276, 382/285, 291, 305, 312, 134; 600/443, 483; 378/21
See application file for complete search history.

(56) References Cited

U.S. PATENT DOCUMENTS

| | | | | |
|---|---|---|---|---|
| 8,009,887 | B2* | 8/2011 | Ionasec et al. | 382/128 |
| 2005/0281447 | A1* | 12/2005 | Moreau-Gobard et al. | 382/130 |
| 2008/0085043 | A1* | 4/2008 | Watanabe et al. | 382/131 |
| 2009/0136106 | A1* | 5/2009 | Roberts et al. | 382/130 |
| 2010/0185091 | A1* | 7/2010 | Sumi et al. | 600/443 |

FOREIGN PATENT DOCUMENTS

| | | |
|---|---|---|
| JP | 2010-188118 | 9/2010 |
| JP | 2011-504629 | 2/2011 |
| JP | 2011-130825 | 7/2011 |
| JP | 2011-239889 | 12/2011 |
| WO | 2006-068271 A1 | 6/2006 |

OTHER PUBLICATIONS

International Search Report issued Feb. 7, 2012, in PCT/JP2011/075330 (with English translation of Category of Cited Documents).
International Search Report issued Feb. 7, 2012, in International Application No. PCT/JP2011/075330 (English translation only).

* cited by examiner

*Primary Examiner* — Seyed Azarian
(74) *Attorney, Agent, or Firm* — Oblon, Spivak, McClelland, Maier & Neustadt, L.L.P.

(57) ABSTRACT

According to one embodiment, an image processing apparatus comprises a storage unit, a specifying unit, a calculation unit, and a display unit. The storage unit stores a three-dimensional image associated with a cardiac region of a subject. The specifying unit specifies a plurality of cardiac valves from a vascular region included in the three-dimensional image by image processing. The calculation unit calculates index values indicating open/close degrees of the cardiac valves. The display unit displays the index values.

10 Claims, 19 Drawing Sheets

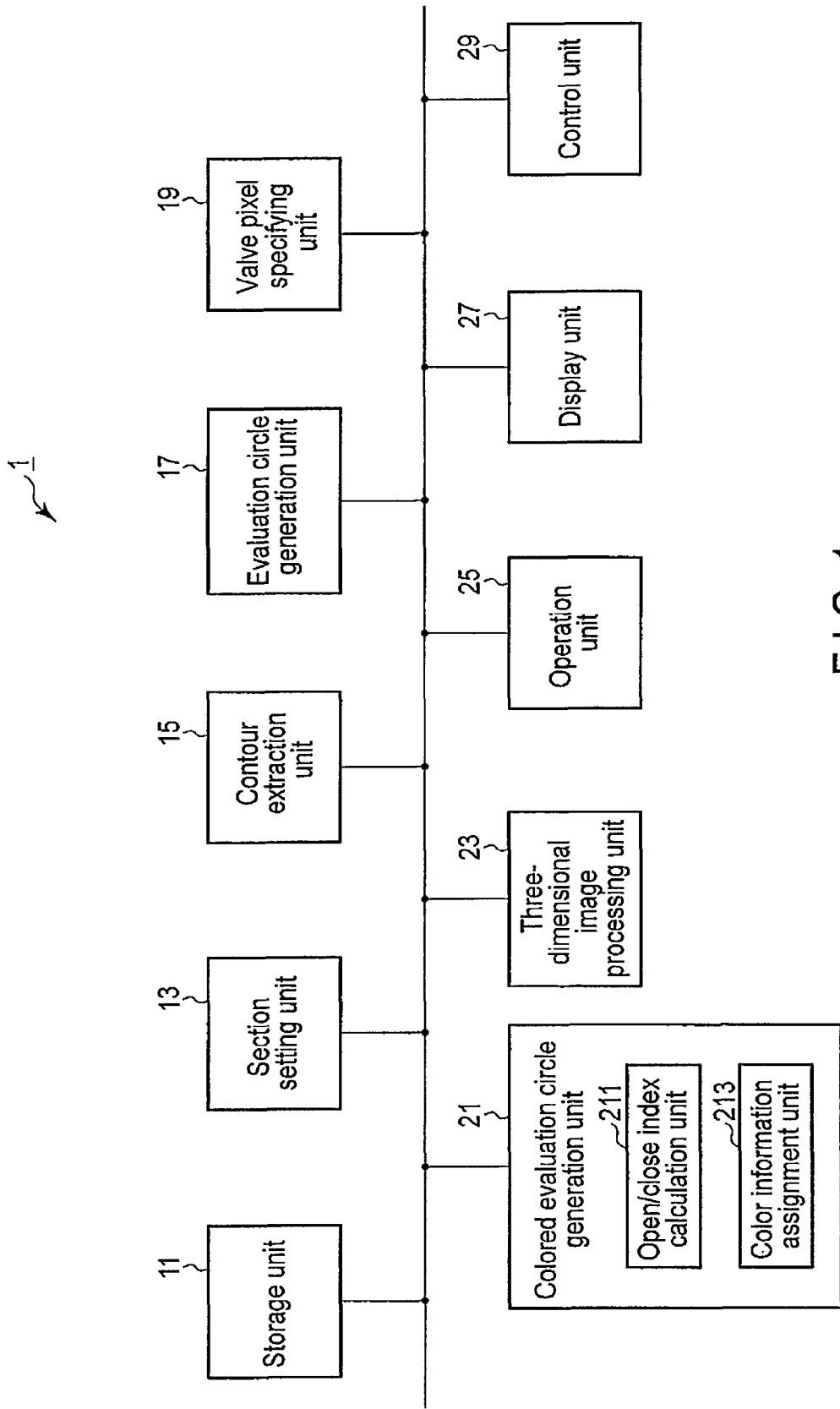
F I G. 1

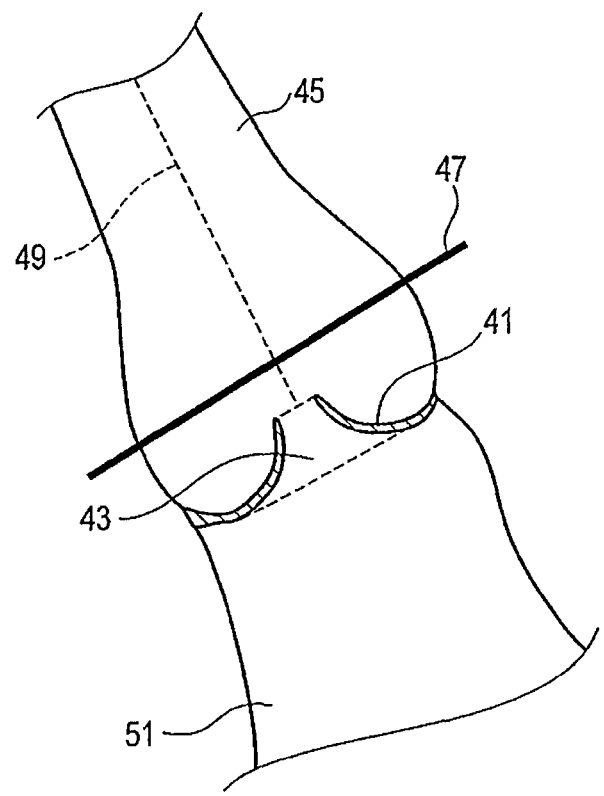
F I G. 6
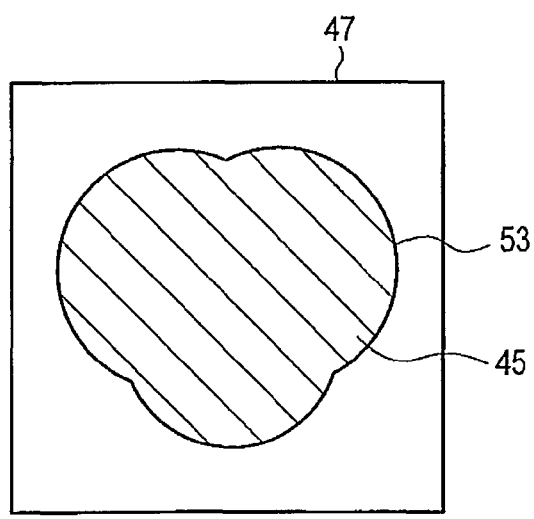
F I G. 7

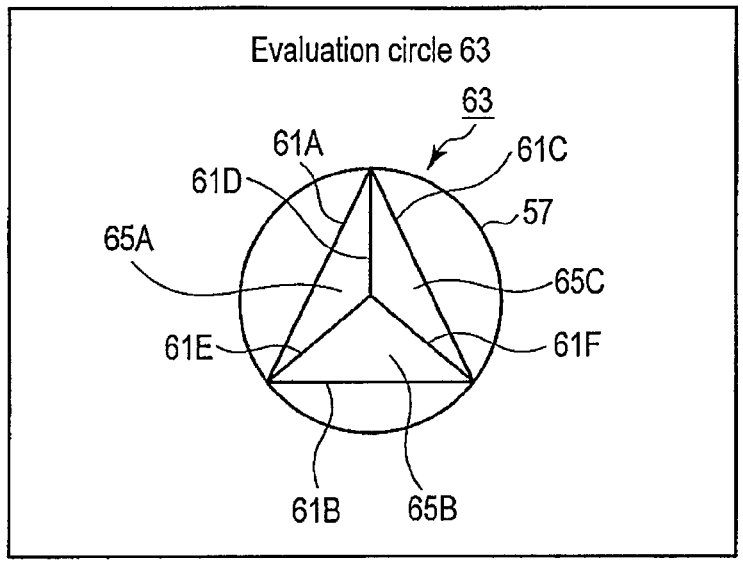
F I G. 10
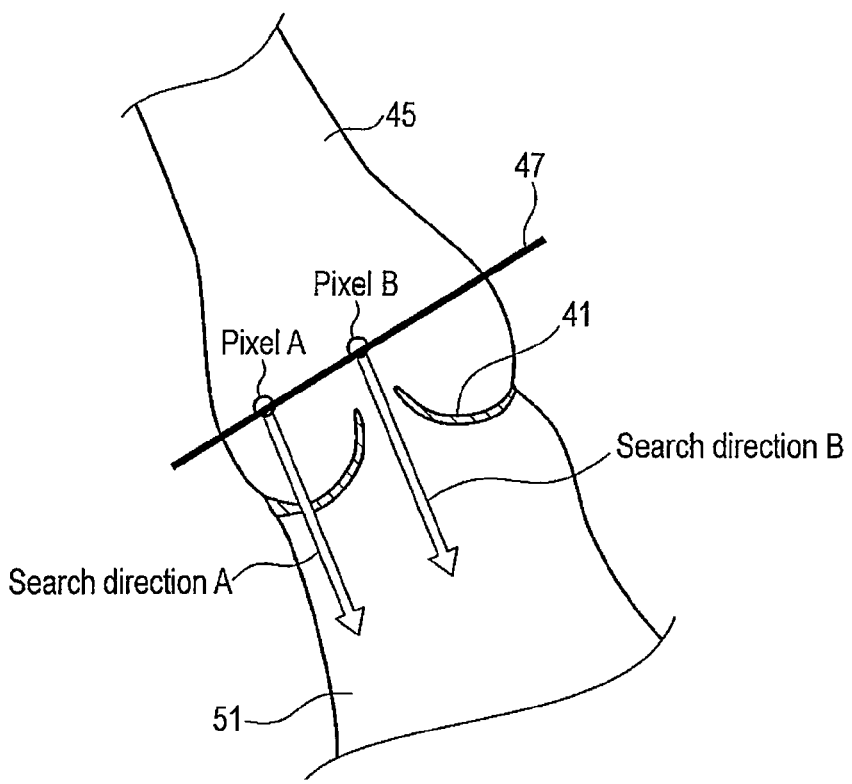
F I G. 11

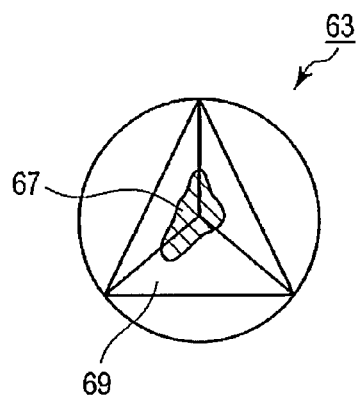
F I G. 12
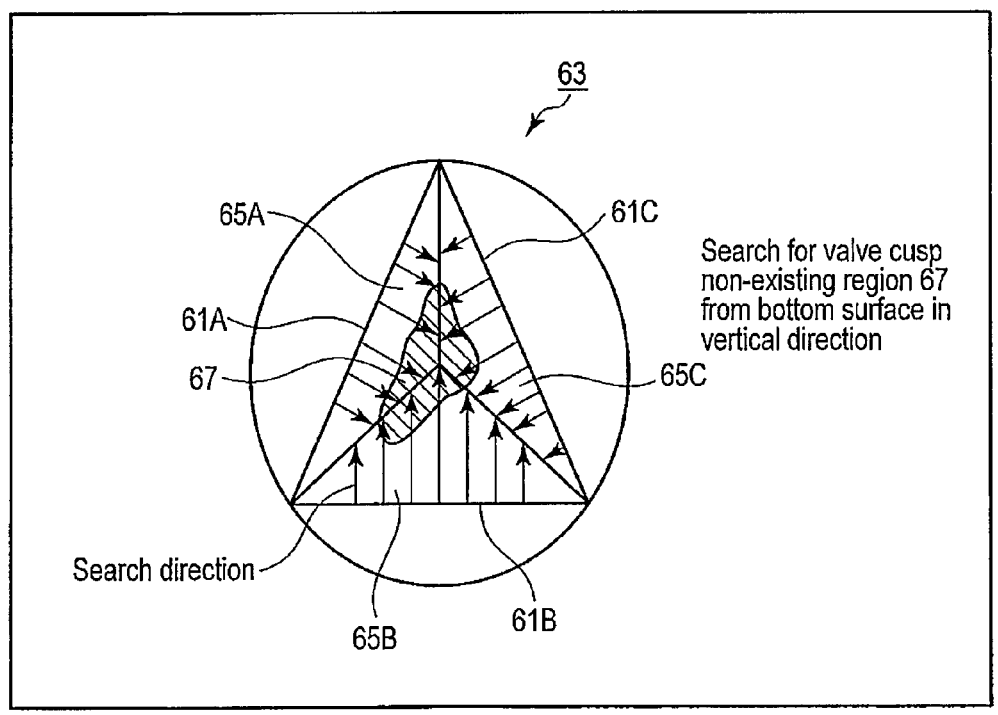
F I G. 13

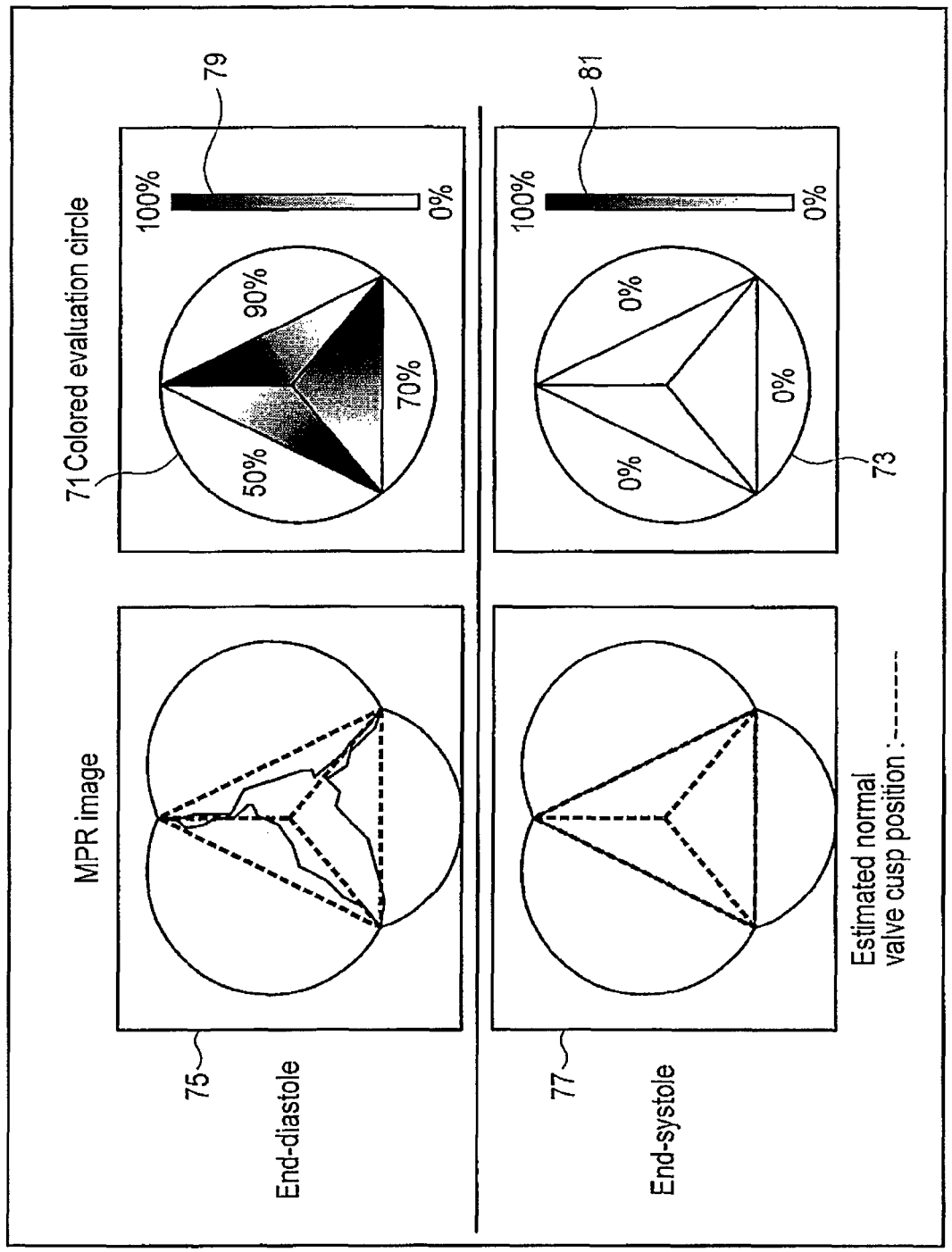
F I G. 14

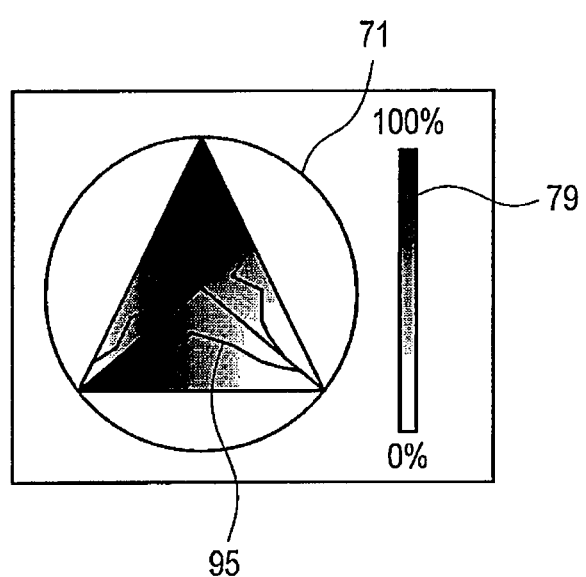
F I G. 16

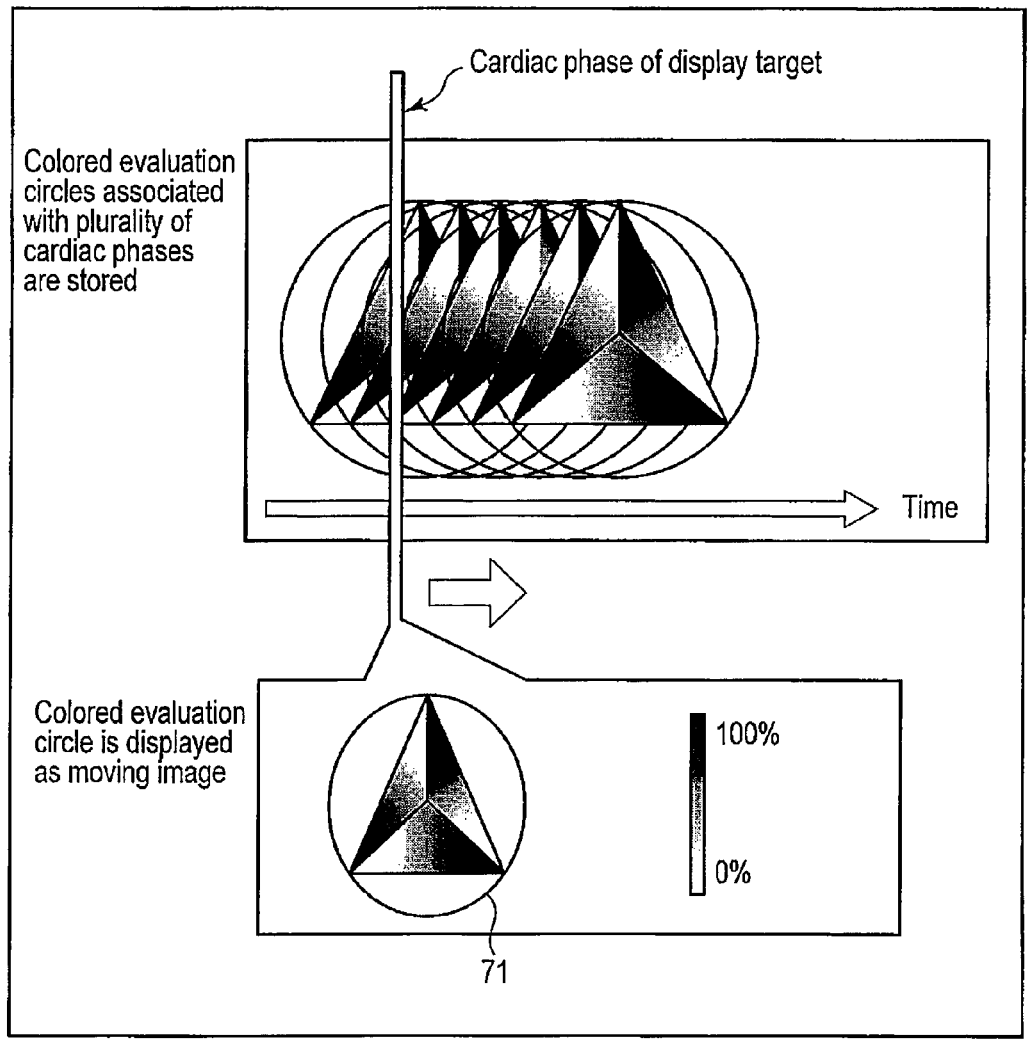
F I G. 19

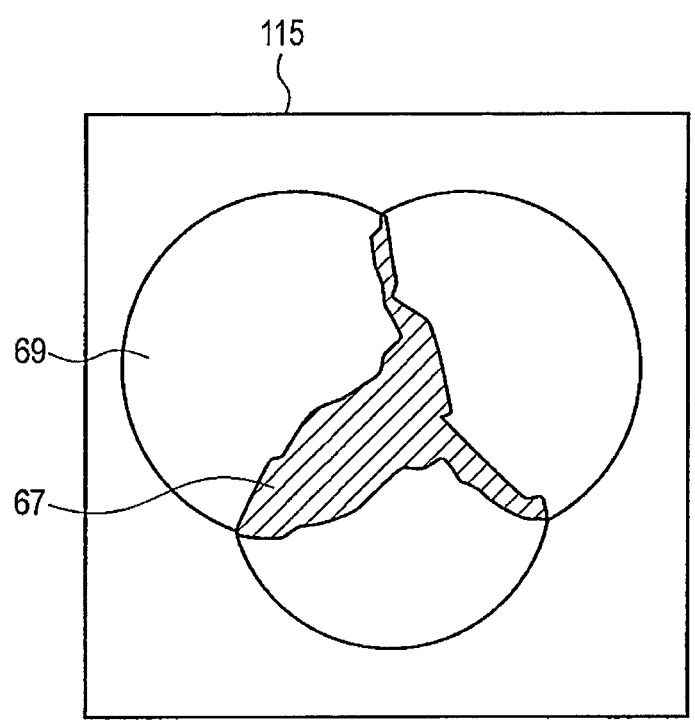
F I G. 21

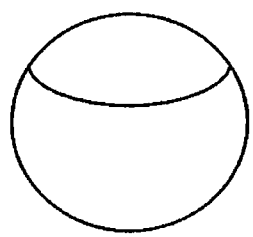
F I G. 24A
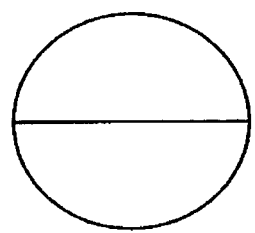
F I G. 24B
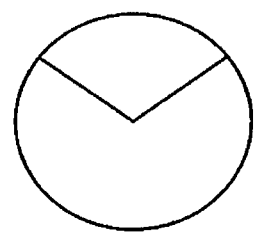
F I G. 24C

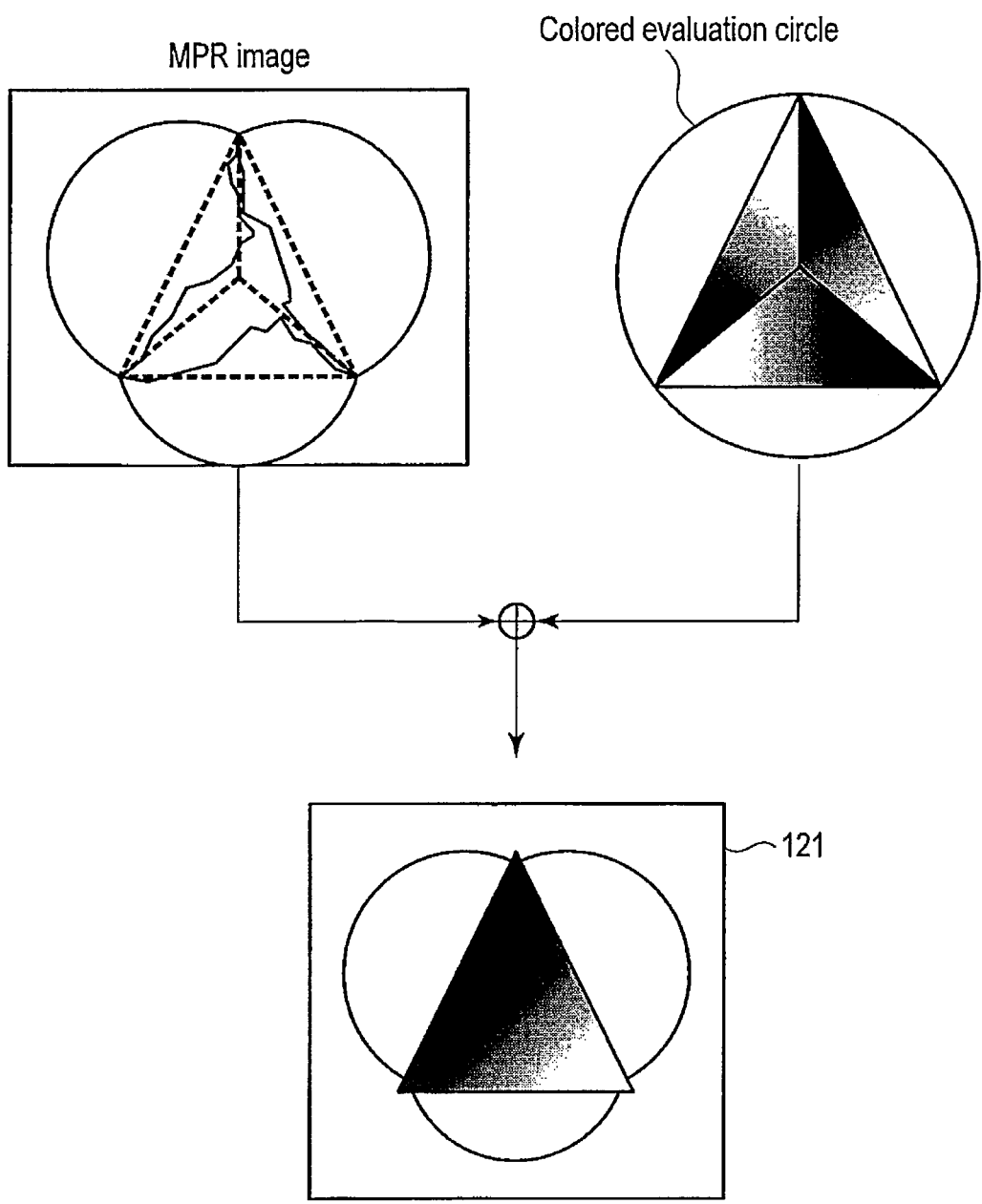
F I G. 25

IMAGE PROCESSING APPARATUS

CROSS REFERENCE TO RELATED APPLICATIONS

This application is a Continuation application of PCT Application No. PCT/JP2011/075330, filed Nov. 2, 2011, the entire contents of which are incorporated herein by reference.

FIELD

Embodiments described herein relate generally to an image processing apparatus.

BACKGROUND

The cardiac valve having a valvular disease does not normally operate. That is, the valve does not completely close or open.

When considering a treatment policy or plan for a valvular disease, a doctor uses a valvular orifice area and the like as information for decision making. For example, when deciding a treatment policy for a valvular disease or making a treatment plan, the doctor visually estimates a valvular orifice area by using three-dimensional image data associated with the cardiac valve, and evaluates the degree of seriousness of a lesion based on the estimated valvular orifice area. There has been no technique established to quantitatively evaluate the behavior of each cardiac valve in deciding a treatment policy or plan for a valvular disease.

It is an object to provide an image processing apparatus which can improve operation efficiency and diagnosis accuracy associated with a valvular disease by a doctor, a technician, and the like.

BRIEF DESCRIPTION OF THE DRAWINGS

FIG. 1 is a block diagram showing the arrangement of an image processing apparatus according to an embodiment.

FIG. 6 is a view for explaining evaluation section setting processing executed by a section setting unit in step S1 in FIG. 5.

FIG. 7 is a view for explaining valvular orifice position vascular contour extraction processing executed by a contour extraction unit in step S2 in FIG. 5.

FIG. 10 is the third view showing a process in evaluation circle generation processing executed by an evaluation circle generation unit in step S3 in FIG. 5.

FIG. 11 is a view for explaining valve pixel specifying processing executed by a valve pixel specifying unit in step S4 in FIG. 5.

FIG. 12 is a view showing an evaluation circle assigned with open information or closed information by the valve pixel specifying unit in step S4 in FIG. 5.

FIG. 13 is a view for explaining open/closed index calculation processing executed by an open/close index calculation unit in step S5 in FIG. 5.

FIG. 14 is a view showing display pattern 1 of colored evaluation circles displayed by a display unit in step S7 in FIG. 5.

FIG. 16 is a view showing display pattern 3 of a colored evaluation circle displayed by the display unit in step S7 in FIG. 5.

FIG. 19 is a view showing display pattern 6 of colored evaluation circles displayed by the display unit in step S7 in FIG. 5.

FIG. 21 is a view showing an example of a colored MPR image displayed by the display unit according to a modification of this embodiment.

FIG. 24A is a view showing an example of an evaluation circle associated with the mitral valve according to the third modification.

FIG. 24B is a view showing an example of an evaluation circle associated with the mitral valve according to the third modification.

FIG. 24C is a view showing an example of an evaluation circle associated with the mitral valve according to the third modification.

FIG. 25 is a view showing an example of display of a combined image according to the fourth modification.

DETAILED DESCRIPTION

In general, according to one embodiment, an image processing apparatus comprises a storage unit, a specifying unit, a calculation unit, and a display unit. The storage unit stores a three-dimensional image associated with a cardiac region of a subject. The specifying unit specifies a plurality of cardiac valves from a vascular region included in the three-dimensional image by image processing. The calculation unit calculates index values indicating open/close degrees of the cardiac valves. The display unit displays the index values.

An image processing apparatus according to an embodiment will be described below with reference to the accompanying drawings.

FIG. 1 is a block diagram showing the arrangement of an image processing apparatus 1 according to this embodiment. The image processing apparatus 1 according to the embodiment handles the cardiac valves as image diagnosis targets. As is well known, the cardiac valves include the aortic valve, the mitral valve, pulmonary valve, and tricuspid valve. This embodiment can be applied to the cardiac valves in all regions. Assume that in order to specifically describe the embodiment below, the cardiac valve to be handled is the aortic valve.

Figure 2:
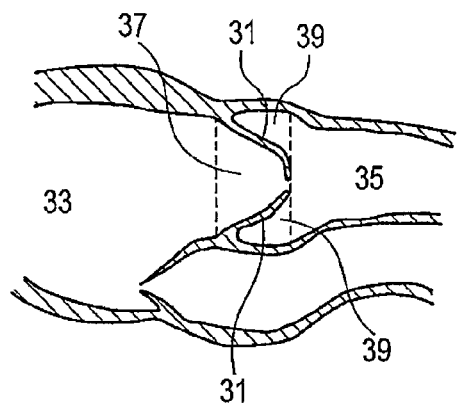
FIG. 2 is a view schematically showing the anatomical structure of the cardiac valve (aortic valve) as an image diagnosis target in this embodiment.

As shown in FIG. 2, an aortic valve 31 is located between a left ventricle 33 and an aorta 35, and functions to prevent regurgitation of blood pumped out from the left ventricle 33. Although FIG. 2 shows only two of the valve cusps of the aortic valve 35, which are actually constituted by three valve cusps. The space surrounded by the three valve cusps 31 is called a valvular orifice 37. The area of the valvular orifice 37 on a section passing through the three valve cusps 31 is called a valvular orifice area. In other words, the area within the valvular orifice contour on the section is the valvular orifice area. The space between each valve cusp 31 and the inner wall of the aorta 35 is called an aortic sinus (so-called the sinus of valsalva) 39.

Figure 3:
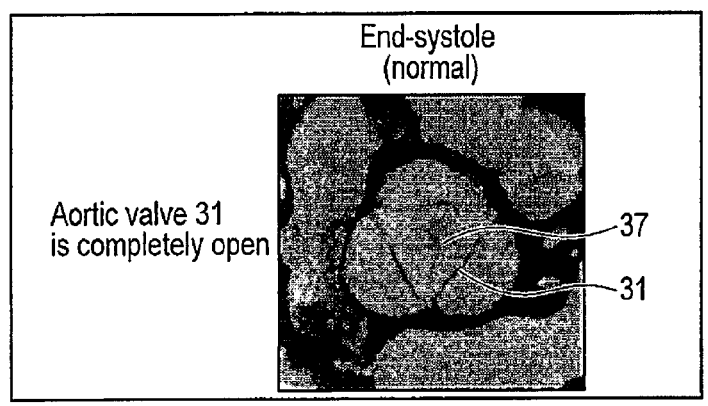
FIG. 3 is a view showing a state in which the aortic valve in FIG. 2 is completely open.
Figure 4:
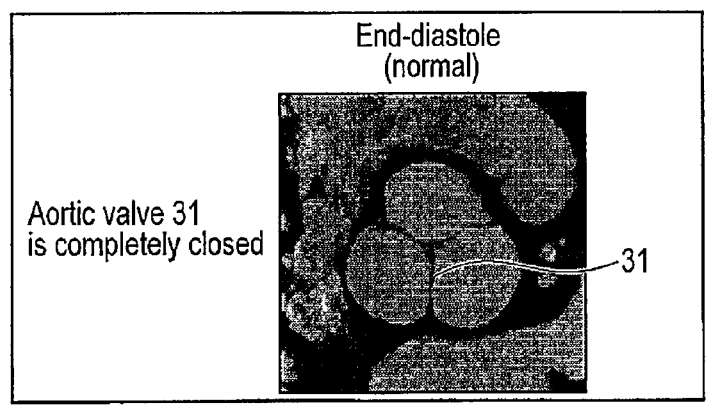
FIG. 4 is a view showing a state in which the aortic valve in FIG. 2 is completely closed.

As shown in FIG. 3, when the left ventricle contracts (for example, at end-systole), the normal aortic valve 31 opens. When the left ventricle relaxes (for example, at an end-diastole), the normal aortic valve 31 closes, as shown in FIG. 4.

The aortic valve with a valvular disease does not normally operate. That is, the valve does not completely close or open. For example, in the case of valve stenosis, the aortic valve does not completely open even at end-systole. In the case of obstruction failure, the aortic valve does not completely close even at an end-diastole. That is, a valvular orifice area can be one index for evaluating whether the heart has suffered from valvular disease.

As shown in FIG. 1, the image processing apparatus 1 includes a storage unit 11, a section setting unit 13, a contour extraction unit 15, an evaluation circle generation unit 17, a valve pixel specifying unit 19, a colored evaluation circle generation unit 21, a three-dimensional image processing unit 23, an operation unit 25, a display unit 27, and a control unit 29.

The storage unit 11 stores the data of a three-dimensional image (volume data) associated with a cardiac region of a subject. The data of three-dimensional images are acquired by diagnostic modalities such as an X-ray computed tomography apparatus, magnetic resonance imaging apparatus, X-ray diagnostic apparatus, and ultrasonic diagnostic apparatus. For a concrete description, assume that a diagnostic modality for acquiring the data of three-dimensional images is an X-ray computed tomography apparatus. The X-ray computed tomography apparatus dynamically scans, for example, the heart contrast-enhanced by a contrast agent with X-rays, and acquires the data of a plurality of three-dimensional images associated with a plurality of cardiac phases corresponding to at least one heartbeat. The storage unit 11 stores the data of three-dimensional images in association with cardiac phases.

The section setting unit 13 sets, in a three-dimensional image, a section (to be referred to as an evaluation section hereinafter) crossing a vascular region of an aortic portion which is contrast-enhanced by image processing or a contrast agent in accordance with an instruction from the user via the operation unit 25. In other words, an evaluation section is set near the valvular orifice or aortic sinus.

The contour extraction unit 15 extracts the contour of the vascular region (to be referred to as the valvular orifice position vascular contour hereinafter) from the vascular region on the evaluation section.

The evaluation circle generation unit 17 generates an aortic valve template (to be referred to as an evaluation circle hereinafter) schematically expressing the shape of the aortic valve based on the valvular orifice position vascular contour. An evaluation section is an image formed by drawing, on an evaluation section, the shape of the normal aortic valve in an open state and the shape of the normal aortic valve in a closed state.

The valve pixel specifying unit 19 searches each pixel constituting the evaluation circle along a predetermined direction for a pixel associated with the aortic valve (to be referred to as a valve pixel hereinafter) included in a three-dimensional image, thereby specifying whether there is a valve pixel. The predetermined direction is set to a direction perpendicular to a section. Information indicating whether there is a valve pixel will be referred to as valve open/close information hereinafter. That is, the valve pixel specifying unit 19 generates valve open/close information for each pixel constituting a section.

The colored evaluation circle generation unit 21 generates an image (to be referred to as a colored evaluation circle hereinafter) expressing the open/close degree of the aortic valve of the subject for each pixel in color. More specifically, the colored evaluation circle generation unit 21 includes an open/close index calculation unit 211 and a color information assignment unit 213. The open/close index calculation unit 211 calculates an index (to be referred to as an open/close index hereinafter) indicating the open/close degree of the aortic valve of a subject. An open/close index indicates, for example, the degree of difference between the open/close degree of the aortic valve of the subject and the open/close degree of the normal aortic valve. The color information assignment unit 213 assigns color information corresponding to the calculated open/close index to each pixel on an evaluation circle to generate a colored evaluation circle.

The three-dimensional image processing unit 23 generates the data of a two-dimensional CT image by performing three-dimensional image processing for the data of a three-dimensional image. As three-dimensional image processing, for example, MPR (Multi Planar Reconstruction) or volume rendering is used. For example, the three-dimensional image processing unit 23 generates the data of an MPR image associated with an evaluation section based on the data of a three-dimensional image.

The operation unit 25 accepts various kinds of commands and information inputs from the user. It is possible to use, as the operation unit 25, pointing devices such as a mouse and a trackball, selection devices such as a mode switch, and input devices such as a keyboard, as needed.

The display unit 27 displays a colored evaluation circle, MPR image, volume rendering image, and the like on a display device. As the display unit, for example, a CRT display, liquid crystal display, organic EL display, plasma display, or the like can be used as needed.

The control unit 29 functions as the main unit of the image processing apparatus 1. Upon receiving a request to start quantitative evaluation processing from the operation unit 25, the control unit 29 executes quantitative evaluation processing for the aortic valve by controlling the respective units in the image processing apparatus 1.

Note that the image processing apparatus 1 can use a general-purpose computer apparatus as basic hardware. The image processing apparatus 1 can implement quantitative evaluation processing for the aortic valve by causing a processor (CPU: Central Processing Unit) mounted in the computer apparatus to execute an image processing program. The image processing program is installed in the computer apparatus in advance. Alternatively, the image processing program may be distributed to the computer apparatus 1 by being stored in a removable recording medium such as a magnetic disk, magneto-optical disk, optical disk, or semiconductor memory or may be distributed to the computer apparatus 1 via a network. The distributed image processing program is implemented by being installed in the computer apparatus 1, as needed. Note that some or all of the units described above can be implemented by hardware such as logic circuits. It is also possible to implement the above units by combining hardware and software control.

Figure 5:
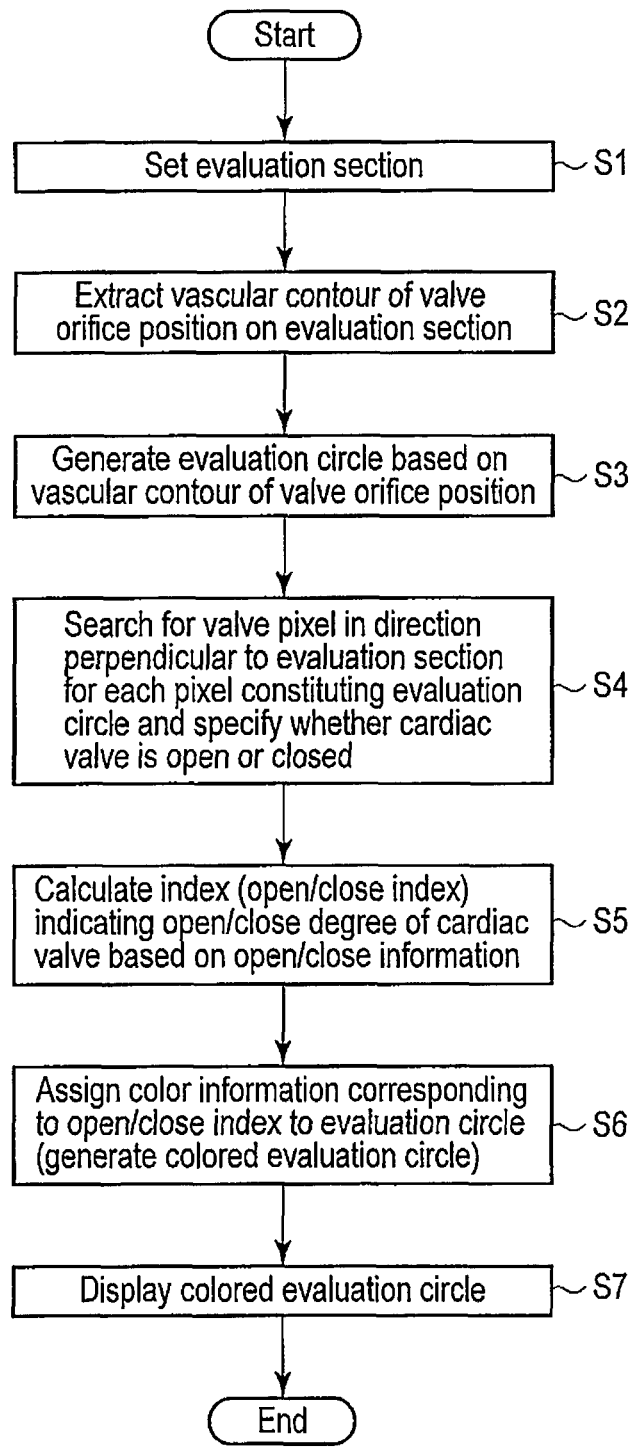
FIG. 5 is a flowchart showing a typical procedure for quantitative evaluation processing of the aortic valve under the control of a control unit in FIG. 2.

An example of the operation of the image processing apparatus 1 will be described next. FIG. 5 is a flowchart showing a typical procedure for quantitative evaluation processing for the aortic valve which is executed under the control of the control unit 29.

Upon receiving an instruction to start quantitative evaluation processing for the aortic valve from the user via the operation unit 25, the control unit 29 reads out the data of a three-dimensional image as a processing target from the data of a plurality of three-dimensional images stored in the storage unit 11. A three-dimensional image as a processing target can be an image corresponding to any cardiac phase. The number of three-dimensional images as processing targets is not limited to one and may be plural. If the number of three-dimensional images is plural, the following processing is performed for each of the images. The user can arbitrarily set a three-dimensional image as a processing target by, for example, designating a cardiac phase via the operation unit 25.

Upon reading out the data of a three-dimensional image, the control unit 29 supplies the readout data of the three-dimensional image to the section setting unit 13, and causes the section setting unit 13 to perform section setting processing (step S1). In step S1, the section setting unit 13 sets an evaluation section in a vascular region in accordance with an instruction from the user via the operation unit 25 or by image processing. The following are concrete examples of section setting processing.

Section Setting Processing 1: The user directly designates the position of an evaluation section via the operation unit 25. For example, as shown in FIG. 6, the user designates a position which is located near an aortic valve region 41 and a valvular orifice region 43 and separated from the valvular orifice region 43 to the deep side of an aortic region 45 by about several mm via the operation unit 25. When the user designates a position, the section setting unit 13 sets an evaluation section 47 so as to include the designated position. For example, the section setting unit 13 sets the evaluation section 47 such that it includes the designated position and is perpendicular to a vascular center line 49. Note that the aortic valve region 41 is a pixel region belonging to the range of CT values which the aortic valve can take. The valvular orifice region 43 is a pixel region belonging to the range of CT values which the blood vessel of the valvular orifice portion contrast-enhanced by a contrast agent can take. The aortic region 45 is a pixel region belonging to the range of CT values which the aortic blood vessel contrast-enhanced by a contrast agent can take. A left ventricle region 51 is a pixel region belonging to the range of CT values which a blood flow channel in the left ventricle contrast-enhanced by a contrast agent can take. That is, the valvular orifice region 43, the aortic region 45, and the left ventricle region 51 belong to almost the same CT value range.

Section Setting Processing 2: The user indirectly designates an evaluation section via the operation unit 25. For example, the user designates the aortic arch in the aortic region which can be easily visually recognized on a CT image. The section setting unit 13 extracts the aortic arch and the left ventricle region from a three-dimensional image by executing region generation processing from the position of the designated aortic arch as a start point. The section setting unit 13 specifies the valvular orifice region from the extracted aortic arch and left ventricle region based on the anatomical structures. The section setting unit 13 sets an evaluation section at a position separated from the specified valvular orifice region to the deep side of the aorta by several mm. In this case as well, the evaluation section is set to be perpendicular to the vascular center line.

If there are a plurality of three-dimensional images as processing targets, a plurality of evaluation sections associated with a plurality of three-dimensional images are set at anatomically the same position or coordinates.

Upon executing step S1, the control unit 29 causes the contour extraction unit 15 to perform contour extraction processing (step S2). In step S2, the contour extraction unit 15 extracts a valvular orifice position blood vessel 53 from the aortic region 45 on the evaluation section 47, as shown in FIG. 7. More specifically, the contour extraction unit 15 extracts the outer contour 53 of the aortic region 45 as a valvular orifice position vascular contour by executing binarization processing for the aortic region 45 on the evaluation section 47. The valvular orifice position vascular contour 53 typically has the shape of the combination of three arcs. The control unit 29 supplies the data of an image of the valvular orifice position vascular contour 53 (to be referred to as a contour image hereinafter) to the evaluation circle generation unit 17.

Figure 8:
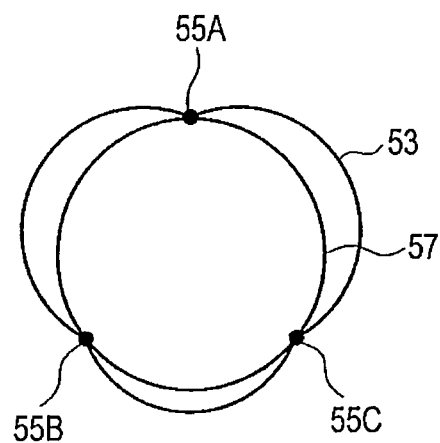
FIG. 8 is the first view showing a process in evaluation circle generation processing executed by an evaluation circle generation unit in step S3 in FIG. 5.
Figure 9:
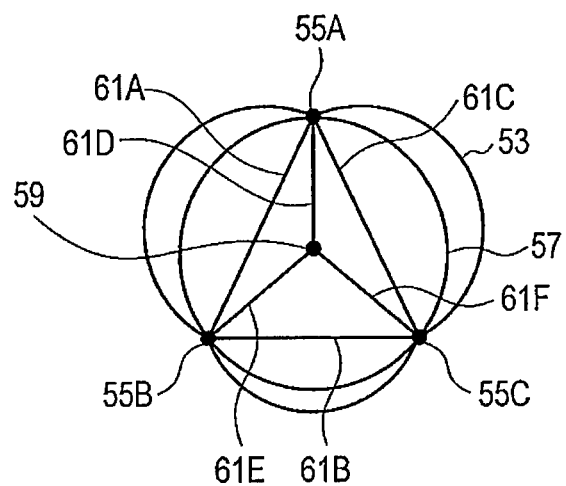
FIG. 9 is the second view showing a process in evaluation circle generation processing executed by an evaluation circle generation unit in step S3 in FIG. 5.

Upon executing step S2, the control unit 29 causes the evaluation circle generation unit 17 to execute evaluation circle generation processing (step S3). In step S3, the evaluation circle generation unit 17 generates an evaluation circle based on the valvular orifice position vascular contour extracted in step S2. First of all, as shown in FIG. 8, the evaluation circle generation unit 17 specifies three cuspidal points 55 on the valvular orifice position vascular contour 53. The cuspidal points 55 are specified in accordance with commands input by the user via the operation unit 25 or by image processing. In this case, the three cuspidal points 55 are cuspidal points 55A, 55B, and 55C. When the three cuspidal points 55 (the cuspidal points 55A, 55B, and 55C) are specified, the evaluation circle generation unit 17 calculates a circle 57 contacting the three specified cuspidal points 55, and draws the calculated circle 57 on a contour image. The circle 57 has the largest diameter among circles falling within the valvular orifice position vascular contour 53. Upon drawing the circle 57, the evaluation circle generation unit 17 draws straight lines 61 (straight lines 61A, 61B, 61C, 61D, 61E, and 61F) connecting all the combinations of two points of a central point 59 of the circle 57 and cuspidal points 55A, 55B, and 55C on the contour image, as shown in FIG. 9. Upon drawing the straight lines 61, the evaluation circle generation unit 17 deletes the valvular orifice position vascular contour from the contour image, as shown in FIG. 10, thereby forming an evaluation circle 63. Note that in the generation processing for the evaluation circle 63, it is not always necessary to delete the valvular orifice position vascular contour, and it is possible to regard the circle on which the valvular orifice position vascular contour remains as an evaluation circle.

A triangle 65A (formed from the straight lines 61A, 61D, and 61E), a triangle 65B (formed from the straight lines 61B, 61E, and 61F), and a triangle 65C (formed from the straight lines 61C, 63F, and 61D) schematically express the shape of the normal valve cusps at end-diastole, as is obvious from the comparison with FIG. 4. The triangle (formed from the straight lines 61A, 61B, and 61C) inscribed to the circle 57 schematically expresses the shape of the normal valve cusps, i.e., the shape of the valvular orifice contour, at end-systole, as is obvious from the comparison with FIG. 3. Assume that in this case, the triangles 65A, 65B, and 65C are estimated normal valve cusps. In this manner, the evaluation circle 63 schematically expresses the estimated shape of the normal cardiac valve in an open state and the estimated shape of the normal cardiac valve in a closed state.

Since the triangles 65A, 65B, and 65C on the evaluation circle are formed based on the actual valvular orifice position vascular contour of the subject, they may have different shapes. In this case, the evaluation circle generation unit 17 may adjust (normalize) the shapes of the triangles 65A, 65B, and 65C so as to make all of them have the same shape.

Upon executing step S3, the control unit 29 causes the valve pixel specifying unit 19 to execute valve pixel specifying processing (step S4). In step S4, as shown in FIG. 11, the valve pixel specifying unit 19 searches each pixel constituting the evaluation circle for a valve pixel included in a three-dimensional image along a predetermined search direction within a limited range, to specify whether there is a valve pixel, i.e., whether the cardiac valve opens or closes. In this case, a valve pixel is a pixel on the aortic valve region 41. A search direction is defined in a direction perpendicular to the section 47 of the evaluation circle (i.e., the evaluation section). It is proper to set the limited range to about 30 mm. Note that the user can arbitrarily set a search direction and a limited range via the operation unit 25. For example, the aortic valve region 41 exists in a limited range extending from a pixel A on the evaluation circle 63 along a search direction A. With regard to the pixel A, therefore, it is specified that there is a valve pixel. In this case, the valve pixel specifying unit 19 assigns close information indicating the presence of a valve pixel to the pixel A on the evaluation circle 63. The aortic valve region 41 does not exist in a limited range extending from a pixel B on the evaluation circle 63 along a search direction B. With regard to the pixel B, therefore, it is specified that there is no valve pixel. The valve pixel specifying unit 19 assigns open information indicating the absence of a valve pixel to the pixel B. In this case, a pixel region assigned with open information will be referred to as a valve cusp non-existing region, whereas a pixel region assigned with close information will be referred to as a valve cusp existing region. Assigning open/close information to the evaluation circle 63 in this manner will provide a valve cusp non-existing region 67 and a valve cusp existing region 69 on the evaluation circle 63, as shown in, for example, FIG. 12.

Upon executing step S4, the control unit 29 causes the open/close index calculation unit 211 of the colored evaluation circle generation unit 21 to execute open/close index calculation processing (step S5). In step S5, the open/close index calculation unit 211 calculates an open/close index for the cardiac valve of the subject based on the open/close information and evaluation circle specified in step S4. The calculated open/close index is stored in the storage unit 11 in association with a cardiac phase. An open/close index is calculated, for example, in the following manner.

As shown in FIG. 13, first of all, the open/close index calculation unit 211 checks the open/closed state of the cardiac valve in the vertical direction from bases 61A, 61B, and 61C of the triangles 65 (the triangles 65A, 65B, and 65O). More specifically, the open/close index calculation unit 211 searches for the valve cusp non-existing region 67 for each unit pixel constituting the bases 61A, 61B, and 61C along the search direction. For example, the search direction is a direction perpendicular to the bases. A unit pixel is a pixel group constituted by a predetermined number (e.g., 10) of consecutive pixels on a base. Note that the user can arbitrarily set a search direction and a unit pixel via the operation unit 25. The open/close index calculation unit 211 calculates an open/close index based on the search result. An open/close index is calculated based on the unit pixel on a base, a shortest distance x to a side facing the base, and a shortest distance y from a pixel on the base to a valve cusp non-existing region along the search direction. More specifically, an open/close index z is an index calculated based on equation (1) given below, and is expressed in percentage.

$$Z=(y/x)\cdot 100 \qquad (1)$$

If no valve cusp non-existing region is found, y=x. When, therefore, the aortic valve is completely closed, open/close index z=100%. When the aortic valve is completely open, y=0, and open/close index z=0%.

The open/close index calculation unit 211 may calculate an open/close index for each triangle 65. An open/close index for each triangle 65 is the simple average value of open/close indices corresponding to a plurality of unit pixels on the base of each triangle as a calculation target or a weighted average value corresponding to a position on the base.

Note that an open/close index is not limited to that defined by equation (1) described above as long as it represents the degree of difference between the open/close degree of the aortic valve of the subject and the open/close degree of the normal aortic valve. For example, an open/close index may be expressed by the simple ratio between the shortest distance x and the shortest distance y. In addition, an open/close index may be calculated based on the difference between the shortest distance x and the shortest distance y (the positional shift amount between the normal valve cusp contour and the actual valve cusp contour) or may be expressed in distance, for example, in mm or pixel as a unit. Alternatively, an open/close index may be simply expressed by the shortest distance y in, for example, mm or pixel as a unit.

Upon executing step S5, the control unit 29 causes the color information assignment unit 213 of the colored evaluation circle generation unit 21 to execute color information assignment processing (step S6). In step S6, the color information assignment unit 213 plots the calculated open/close indices on the corresponding pixels on the evaluation circle. More specifically, the color information assignment unit 213 holds a table which associates open/close indices with color information. The color information assignment unit 213 specifies color information associated with a calculated open/close index on the table, and plots the specified color information to the pixel as an assignment target. A pixel as an assignment target is a pixel on an evaluation circle and is a pixel on a search path when the open/close index is calculated. That is, one piece of color information is assigned onto one search path. If bases differ in position, different pieces of color information may be assigned.

Upon executing step S6, the control unit 29 causes the display unit 27 to execute display processing (step S7). In step S7, the display unit 27 displays a colored evaluation circle in a preset display pattern. The display unit 27 prepares various display patterns for improving the open/close degree evaluation accuracy/efficiency. Concrete display patterns of colored evaluation circles by the display unit 27 will be described below.

Display Pattern 1: FIG. 14 is a view showing display pattern 1 of a colored evaluation circle by the display unit 27. As shown in FIG. 14, the display unit 27 displays a colored evaluation circle 71 associated with end-diastole in one heartbeat or a colored evaluation circle 73 associated with end-systole, or simultaneously displays both the colored evaluation circles 71 and 73. For example, the display unit 27 specifies the colored evaluation circle 71 corresponding to end-diastole as a circle having the largest valvular orifice area among a plurality of colored evaluation circles corresponding to one heartbeat, and the colored evaluation circle 73 corresponding to en-systole as a circle having the smallest valvular orifice area among a plurality of colored evaluation circles corresponding to one heartbeat. Note that end-diastole or end-systole can be arbitrarily set via the operation unit 25. In addition, the display unit 27 preferably displays an MPR image 75 corresponding to end-diastole on a side of the colored evaluation circle 71, and an MPR image 77 corresponding to end-systole on a side of the colored evaluation circle 73. The three-dimensional image processing unit 23 generates the MPR images 75 and 77. The MPR images 75 and 77 are associated with the same section (i.e., the evaluation section set in step S1) as that with which the colored evaluation circles 71 and 73 are associated. To also visually evaluate open/close degrees on the MPR images 75 and 77, the display unit 27 preferably superimposes and displays the triangle contours (estimated normal valve cusp positions), displayed on the colored evaluation circles 71 and 73, on the MPR images 75 and 77.

As shown in FIG. 14, the colored evaluation circles 71 and 73 express the spatial distributions of the open/close degrees of the aortic valve in different colors. Therefore, the user can comprehend partial open/close degrees of the aortic valve in different colors by observing the colored evaluation circles 71 and 73. This allows the user to intuitively evaluate open/close degrees. In this case, to show the user the correspondence relationship between open/close indices and colors, the display unit 27 preferably displays color bars 79 and 81 indicating the correspondence relationship between open/close indices and colors near the colored evaluation circles 71 and 73. In addition, the display unit 27 preferably displays the open/close degrees of the triangles (e.g., average open/close indices within the triangles) calculated in step S5 near the respective triangles in the colored evaluation circles 71 and 73. For example, in the colored evaluation circle 71 corresponding to end-diastole, 50%, 90%, and 70% are respectively displayed near the left triangle, the right triangle, and the lower triangle. Displaying the open/close degrees of the triangles in this manner allows the user to evaluate the open/close degrees of the cardiac valve not only as colors but also as numbers. Note that the cardiac phases to which colored evaluation circles as display targets of display pattern 1 correspond are not limited to end-diastole and end-systole, and may be arbitrary cardiac phases.

Note that the display unit 27 may display CPR (Curved Planar Reconstruction) images in place of MPR images. The three-dimensional image processing unit 23 generates CPR images by performing CPR processing for three-dimensional images.

Figure 15:
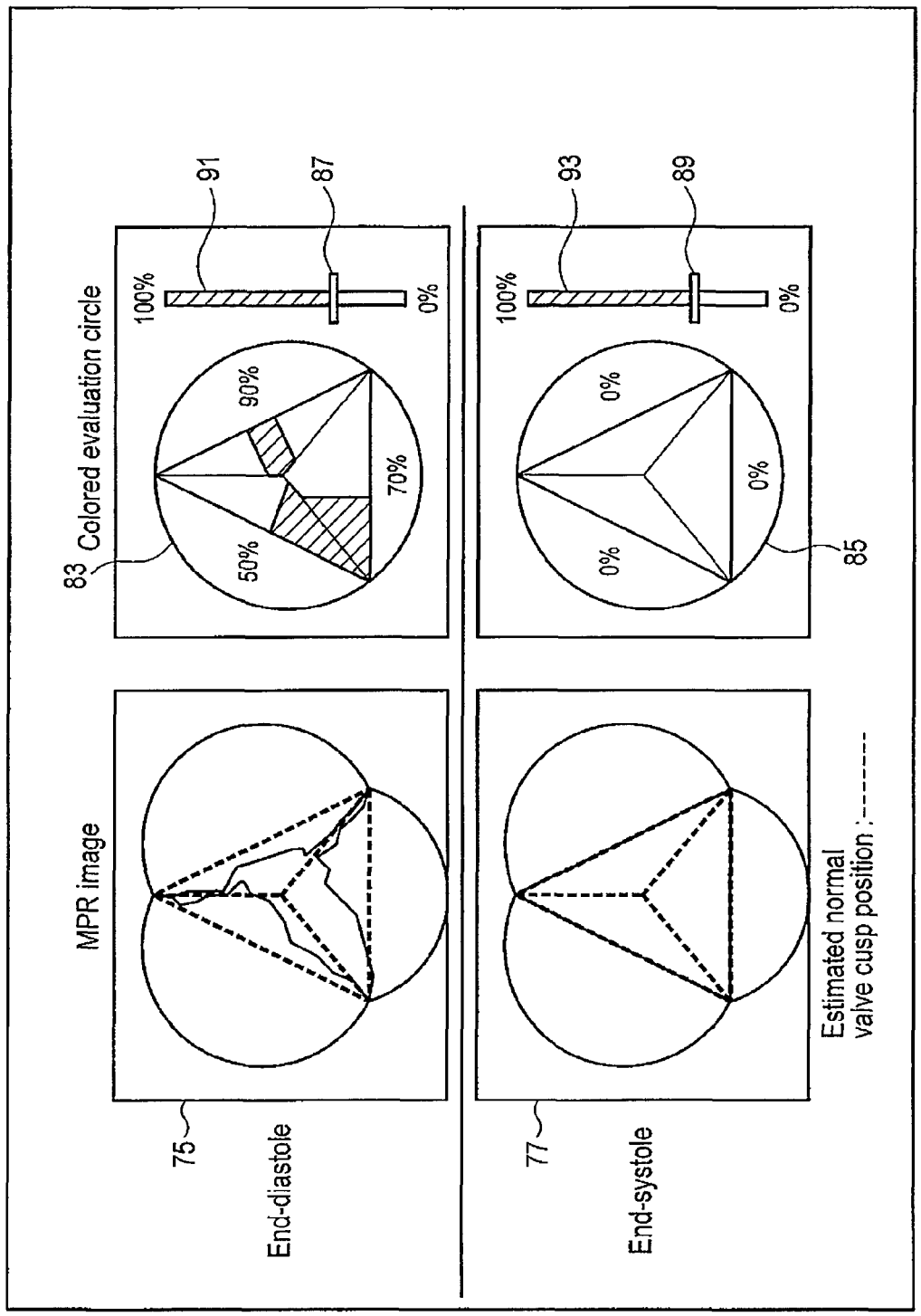
FIG. 15 is a view showing display pattern 2 of colored evaluation circles displayed by the display unit in step S7 in FIG. 5.

Display Pattern 2: FIG. 15 is a view showing display pattern 2 of colored evaluation circles displayed by the display unit 27. As shown in FIG. 15, colored evaluation circles 83 and 85 in display pattern 2 are colored in accordance with magnitude relationships with a threshold. More specifically, a pixel having an open/close index larger than the threshold is displayed in the first color (e.g., red), and a pixel having an open/close index smaller than the threshold is displayed in the second color (e.g., blue). In other words, the color information assignment unit 213 assigns color information corresponding to the first color to a pixel having an open/close index larger than the threshold, and assigns color information corresponding to the second color to a pixel having an open/close index smaller than the threshold. The display unit 27 displays this threshold. For example, the display unit 27 displays sliders 87 and 89, each indicating a threshold, and color bars 91 and 93. In this case, sliding the sliders 87 and 89 on the color bars 91 and 93 via the operation unit 25 will change the threshold to numerical values corresponding to the positions of the sliders 87 and 89. Alternatively, the display unit 27 may simply display a numerical value indicating a threshold. In this case, inputting a numerical value via the operation unit 25 will change the threshold. In display pattern 2, since an evaluation circle is colored in accordance with the magnitude relationship with a threshold, observing the colored evaluation circles 83 and 85 allows to visually and easily comprehend a valve cusp region with a good open/close degree relative to the threshold and a valve cusp region with a bad open/close degree relative to the threshold. Setting a clinically proper threshold can also easily specify a valve cusp region with a dysfunction. Note that the number of thresholds is not limited to one, and may be plural. With an increase in the number of thresholds, the number of display colors of a colored evaluation circle increases. If, for example, two thresholds are set, three display colors are used. Note that the cardiac phases to which colored evaluation circles as display targets of display pattern 2 correspond are not limited to end-diastole and end-systole, and may be arbitrary cardiac phases.

Display Pattern 3: FIG. 16 is a view showing display pattern 3 of a colored evaluation circle displayed by the display unit 27. As shown in FIG. 16, in the case of display pattern 3, the display unit 27 superimposes and displays a contour of a valve cusp region (to be referred to as a valve cusp contour hereinafter) 95 associated with the same cardiac phase as that of the evaluation circle on the colored evaluation circle 71. The contour extraction unit 15 extracts the valve cusp contour 95 from an MPR image associated with an evaluation section. Displaying the valve cusp contour 95 on the colored evaluation circle 71 in this manner allows the user to evaluate the open/close degree of the cardiac valve more easily and accurately. This also improves the reliability of evaluation of an open/close degree. Note that a colored evaluation circle as a display target of display pattern 3 is not limited to a colored evaluation circle corresponding to end-diastole. That is, this display pattern can be applied to colored evaluation circles corresponding to arbitrary cardiac phases. The display unit 27 may display a plurality of valve cusp contours associated with a plurality of cardiac phases on one colored evaluation circle.

Figure 17:
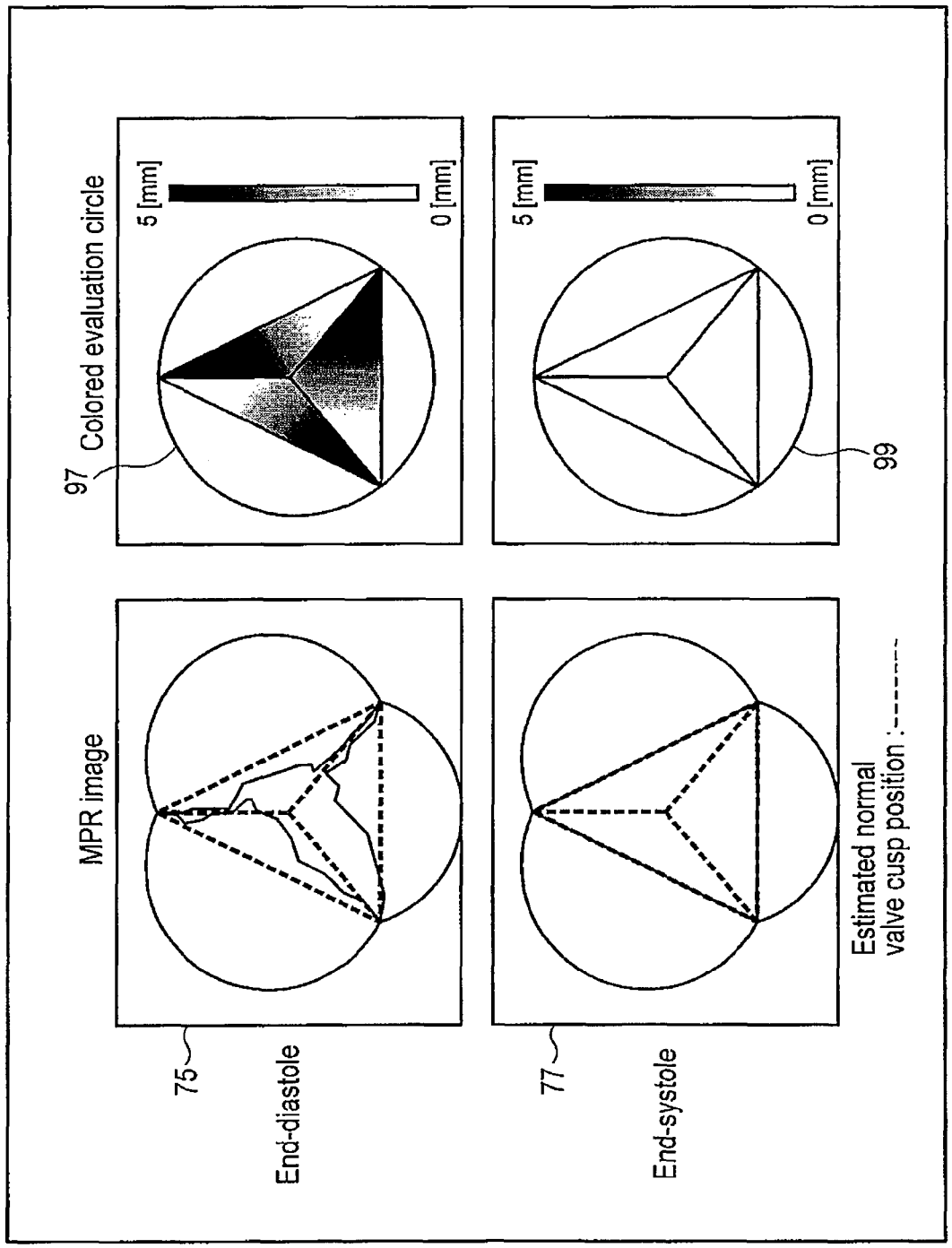
FIG. 17 is a view showing display pattern 4 of colored evaluation circles displayed by the display unit in step S7 in FIG. 5.

Display Pattern 4: FIG. 17 is a view showing display pattern 4 of colored evaluation circles displayed by the display unit 27. As shown in FIG. 17, colored evaluation circles 97 and 99 in display pattern 4 are displayed in colors corresponding to positional shift amounts relative to the normal valve cusp contour (the differences between the shortest distances x and y in equation (1)). Positional shift amounts are displayed in millimeters [mm].

Figure 18:
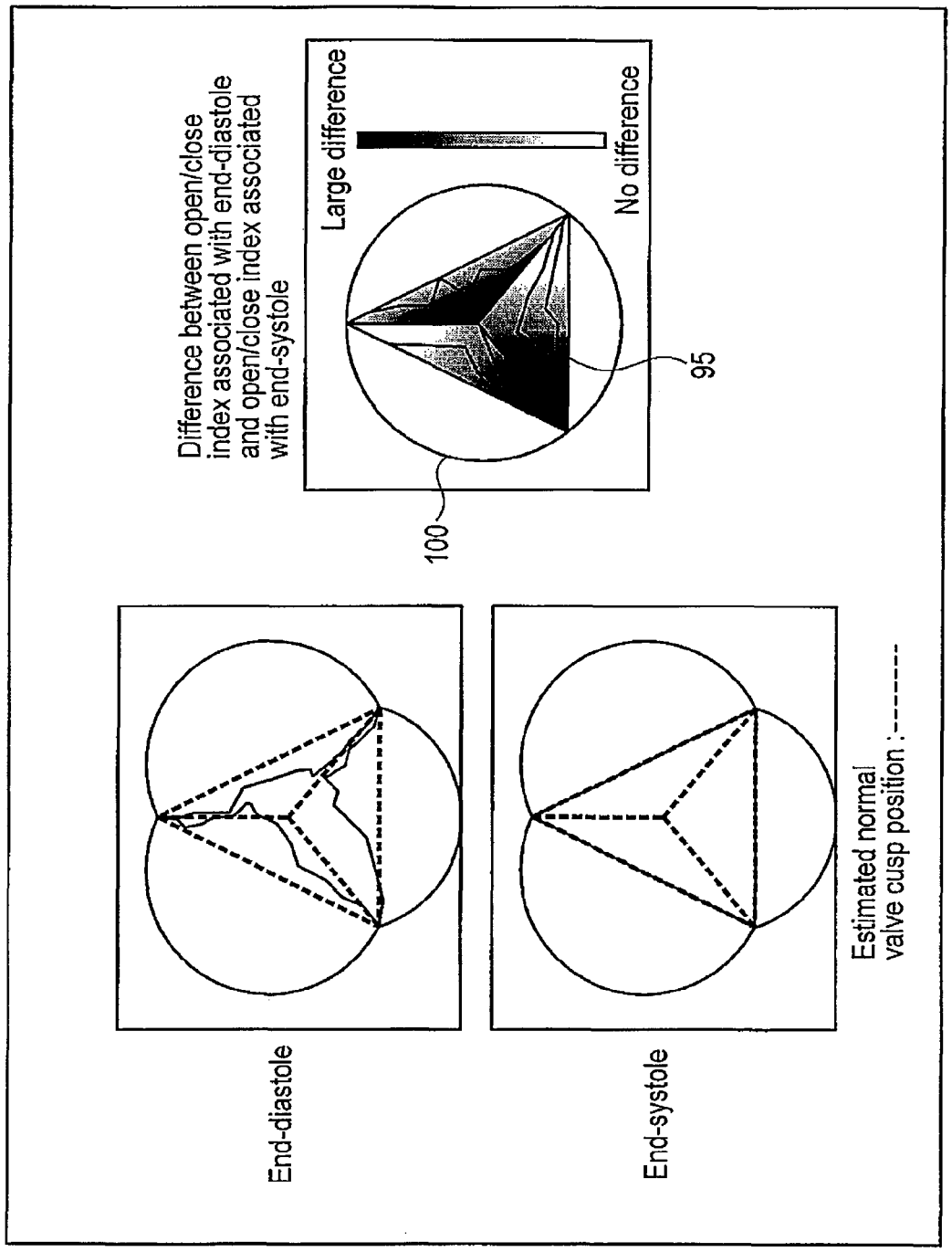
FIG. 18 is a view showing display pattern 5 of a colored evaluation circle displayed by the display unit in step S7 in FIG. 5.

Display Pattern 5: FIG. 18 is a view showing display pattern 5 of colored evaluation circles displayed by the display unit 27. As shown in FIG. 18, a colored evaluation circle 100 in display pattern 5 is colored in accordance with the differences between open/close indices in different two cardiac phases. For example, the two different cardiac phases are phases in one heartbeat in which the open area becomes minimum and maximum, respectively. A phase in which the open area becomes minimum is typically end-diastole, and a phase in which the open area becomes maximum is typically end-systole. An open area corresponds to the number of pixels (area) constituting a valve cusp existing region of an evaluation circle. In order to improve the diagnosis accuracy, the display unit 27 may display an MPR image corresponding to a phase in which the open area becomes minimum and an MPR image corresponding to a phase in which the open area becomes maximum, on a side of the colored evaluation circle 100. In addition, in order to improve the diagnosis accuracy, the display unit 27 may superimpose the center line contour 95 included in the displayed MPR image on the colored evaluation circle 100. In the case of FIG. 18, the display unit 27 superimposes the valve cusp contour 95 associated with a phase in which the open area is minimum (i.e., end-diastole) and the valve cusp contour 95 associated with a phase in which the open area is maximum (i.e., end-systole).

Using display patterns 1 to 5 allows the user to easily quantitatively evaluate the behavior of the cardiac valve by observing the displayed colored evaluation circle associated with a cardiac phase. Therefore, the image processing apparatus 1 can improve the operation efficiency and diagnosis accuracy of the user when deciding a treatment policy for a valvular disease or making a treatment plan.

Display Pattern 6: FIG. 19 is a view showing display pattern 5 of colored evaluation circles displayed by the display unit 27. As shown in FIG. 19, in the case of display pattern 6, the display unit 27 displays a plurality of colored evaluation circles associated with a plurality of cardiac phases as a moving image. More specifically, colored evaluation circles associated with a plurality of cardiac phases corresponding to at least one heartbeat are generated and stored in the storage unit 11 under the control of the control unit 29. The display unit 27 displays the colored evaluation circles stored in the storage unit 11 in chronological order as a moving image. In this case, colored evaluation circles may be displayed together with a color bar, as described above. The display speed can be low playback speeds such as 0.5× speed or high playback speeds such as 2× speed as well as the normal speed, i.e., 1× speed. The display speed can be arbitrarily changed via the operation unit 25. The display of a moving image allows the user to comprehend temporal changes in the open/close degree of the cardiac valve as changes in color. In addition, upon receiving an instruction to stop the display of a moving image via the operation unit 25, the display unit 27 can stop the display of the moving image and keep displaying the colored evaluation circle displayed at the time when the stop instruction is issued. Note that colored evaluation circles in display pattern 6 are compatible with any of display patterns 1 to 5.

Figure 20:
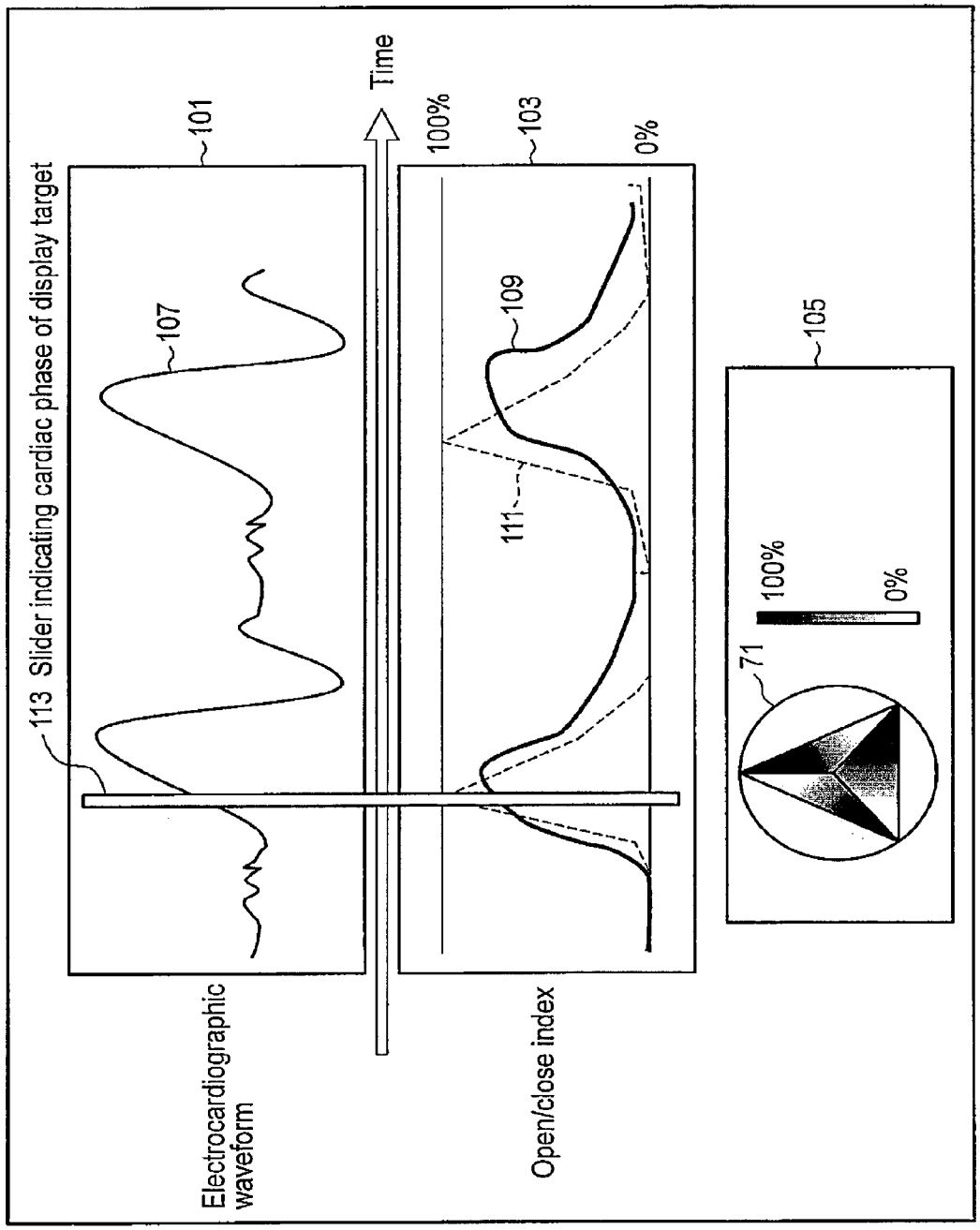
FIG. 20 is a view showing display pattern 7 of a colored evaluation circle displayed by the display unit in step S7 in FIG. 5.

Display Pattern 7: FIG. 20 is a view showing display pattern 7 of a colored evaluation circle displayed by the display unit 27. As shown in FIG. 20, in the case of display pattern 7, the display unit 27 displays an electrocardiographic waveform and an open/close index waveform together with a colored evaluation circle as a moving image. More specifically, a display area 101 for an electrocardiographic waveform 107, a display area 103 for an open/close index waveform 109, and a display area 105 for the colored evaluation circle 71 are arranged in a display window. The display area 103 may display not only the open/close index waveform 109 associated with the subject but also an open/close index waveform 111 associated with an able-bodied person for the comparison between the able-bodied person and the subject. The waveform 111 may be generated in the above step, or calculated theoretically, or generated empirically. Note that the abscissa of each of the open/close index waveforms 109 and 111 represents the time, and the ordinate the open/close index.

It is convenient for the evaluation of an open/close index to know a specific position on the electrocardiographic waveform 107 or the open/close index waveform 109 or 111 to which the cardiac phase corresponding to a displayed colored evaluation circle corresponds. As described above, the colored evaluation circle 71 and the open/close index are stored in the storage unit 11 in association with the cardiac phase. By using this associating operation, the display unit 27 superimposes and displays a slider 113 indicating a cardiac phase corresponding to the colored evaluation circle 71 on the electrocardiographic waveform 107 and the open/close index graphs 109 and 111. The slider 113 is moved along the abscissas of the electrocardiographic waveform 107 and open/close index waveforms 109 and 111 upon switching of the colored evaluation circle 71 to be displayed. Note that the colored evaluation circle 71 in display pattern 7 is compatible with any of display patterns 1 to 5.

Using display patterns 6 and 7 allows the user to decide a treatment policy for a valvular disease or make a treatment plan in consideration of the open/close degrees associated with a plurality of cardiac phases. If a given case is regarded as serious in one cardiac phase but regarded as mild in a plurality of cardiac phases, this technique allows to consider whether treatment is required.

Therefore, the image processing apparatus according to this embodiment can improve operation efficiency and diagnosis accuracy associated with a valvular disease by a doctor, a technician, and the like.

Note that the present invention is not limited to the embodiment described above, and constituent elements can be modified and embodied in the execution stage within the spirit and scope of the invention.

(First Modification)

As shown in FIG. 21, the display unit 27 according to the first modification displays a colored MPR image 115. The colored MPR image 115 is an MPR image assigned with color information corresponding to the open/close information specified in step S4 by the color information assignment unit 213. A method of generating the colored MPR image 115 will be described below.

First of all, the valve pixel specifying unit 19 maps, on an MPR image associated with an evaluation section, information indicating whether there is a valve pixel. More specifically, the valve pixel specifying unit 19 specifies, for the pixels of an MPR image associated with an evaluation section, whether the cardiac valve is open or closed (that is, whether there is a valve pixel in a direction perpendicular to the evaluation section) in the same method as in step S4. The valve pixel specifying unit 19 assigns close information to a pixel specified as the presence of a valve pixel, and assigns open information to a pixel specified as the absence of a valve pixel. Upon assignment of open information and close information to the MPR image, a coloring information assignment unit 33 assigns color information corresponding to open information to each pixel assigned with open information, and assigns color information corresponding to close information to each pixel assigned with close information. This generates the colored MPR image 115. The display unit 27 then displays the colored MPR image 115. For example, the pixel region (valve cusp existing region) 67 assigned with close information is displayed in blue, whereas the pixel region (valve cusp non-existing region) 69 assigned with open information is displayed in red. Displaying the colored MPR image allows the user to determine the three-dimensional open/close state of the cardiac valve in color on the two-dimensional MPR image.

(Second Modification)

An image processing apparatus according to the second modification sets an evaluation section and calculates open/close indices following a procedure different from that shown in FIG. 5. The image processing apparatus according to the second modification will be described below. Note that the same reference numerals in the following description denote constituent elements having almost the same functions and arrangements as in this embodiment, and a repetitive description will be made only when required.

Figure 22:
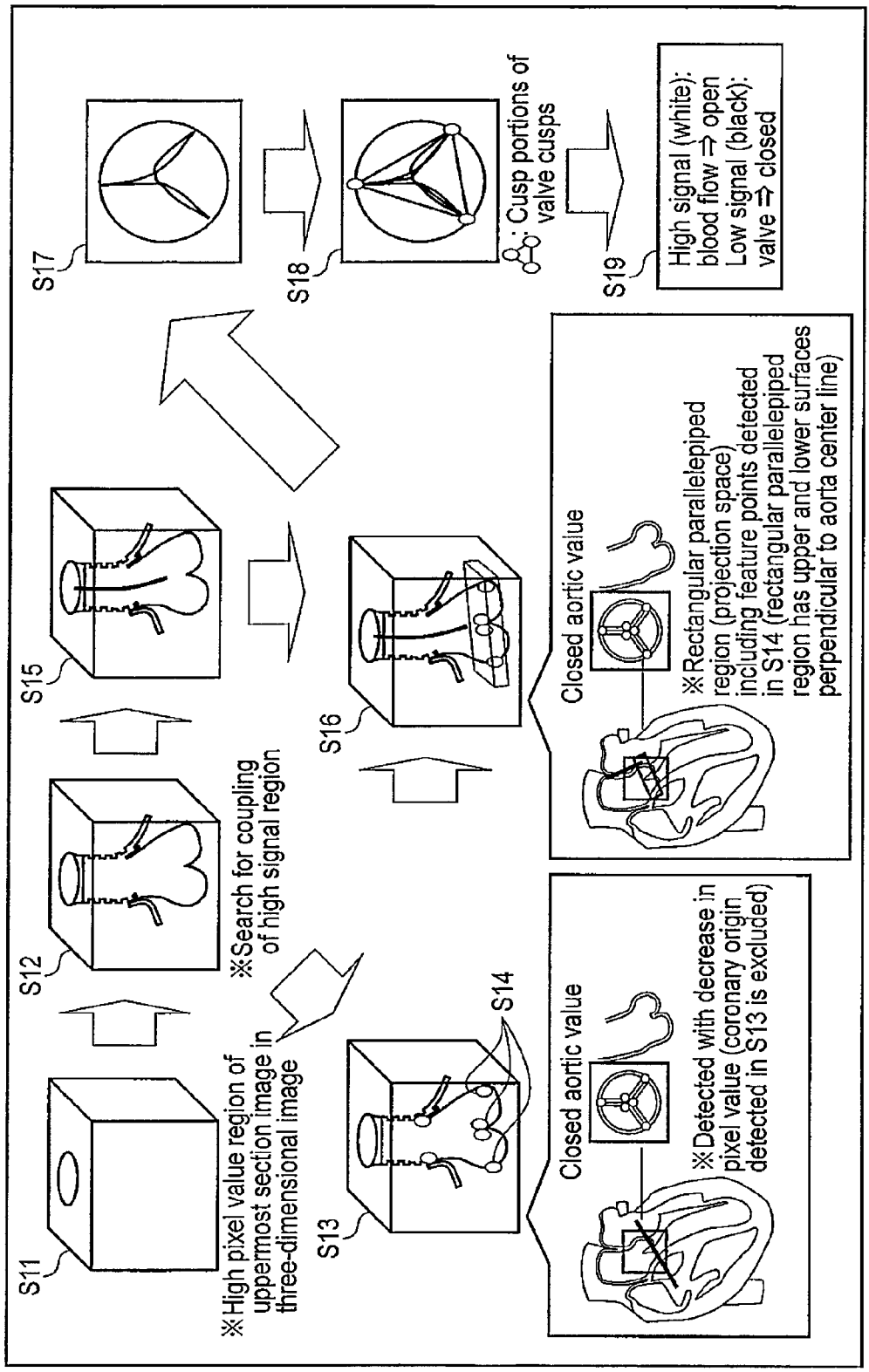
FIG. 22 is a view schematically showing a typical procedure for processing performed by an image processing apparatus according to the second modification.

FIG. 22 is a view schematically showing a procedure for processing according to the second modification. As shown in FIG. 22, first of all, the control unit 29 causes the contour extraction unit 15 to perform detection processing (step S11). In step S11, the contour extraction unit 15 detects the aortic region from a three-dimensional image. More specifically, first of all, the contour extraction unit 15 specifies the uppermost section image (the section image at the maximum or minimum Z-coordinates) of the three-dimensional image. The contour extraction unit 15 then specifies a high pixel region from a plurality of pixels included in the uppermost section image. The specified high pixel region is set as an aortic region.

Upon executing step S11, the control unit 29 causes the contour extraction unit 15 to perform extraction processing (step S12). In step S12, the contour extraction unit 15 extracts an aortic region from the three-dimensional image by using the aortic region detected in step S11 as the origin. More specifically, the contour extraction unit 15 searches for pixels coupled to the aortic region detected in step S11 in terms of pixel values, and extracts pixels to be coupled as an aortic region from the three-dimensional image.

Upon executing step S12, the control unit 29 causes the evaluation circle generation unit 17 to perform specifying processing. In specifying processing, the evaluation circle generation unit 17 searches the pixels of the aortic region downward along the Z-coordinates for pixels having low pixel values in the aortic region. A pixel having a low pixel value is a candidate belonging to cardiac valve region. More specifically, in steps S13 and S14, the control unit 29 causes the evaluation circle generation unit 17 to perform detection processing. In step S13, the evaluation circle generation unit 17 detects two coronary origin points from the aortic region as pixels having low pixel values. The coronary artery region branches from the aortic region. The coronary origin is the branching point between the coronary artery region and the aortic region. The coronary origin is located anatomically closer to the end side of the vascular region than the aortic valve. The coronary origin is excluded from the cardiac valve region. When the coronary origin is detected, the evaluation circle generation unit 17 searches again the pixels of the aortic region for pixels having low pixel values in the aortic region. In step S14, the evaluation circle generation unit 17 detects feature points of the aortic region as pixels having low pixel values. There are six feature points. These feature points are anatomically regarded as feature points of the cardiac valve region.

Upon executing step S12, the control unit 29 causes the evaluation circle generation unit 17 to perform center line extraction processing concurrently in steps S13 and 14 (step S15). In step S15, the evaluation circle generation unit 17 extracts the center line of the aortic region extracted in step S12.

Upon executing steps S14 and S15, the control unit 29 causes the evaluation circle generation unit 17 to perform setting processing (step S16). In step S16, the evaluation circle generation unit 17 sets a three-dimensional region (sub-volume) including the six feature points detected in step S14. For example, a three-dimensional region is set in a rectangular parallelepiped region having upper and lower surfaces perpendicular to the center line. The set three-dimensional region is subjected projection processing in step S17. Therefore, this three-dimensional region will be referred to as a projection space.

Upon executing step S16, the control unit 29 causes the evaluation circle generation unit 17 to perform projection image generation processing (step S17). In step S17, the evaluation circle generation unit 17 performs projection processing for the three-dimensional image within the projection space to generate a projection image. For example, the evaluation circle generation unit 17 performs projection processing along the center line. Projection processing may be any of existing methods such as a maximum value projection method, minimum value projection method, and average value projection method. For example, it is preferable to execute projection processing by the minimum value projection method.

Upon executing step S17, the control unit 29 causes the evaluation circle generation unit 17 to perform evaluation circle generation processing (step S18). In step S18, the evaluation circle generation unit 17 generates an evaluation circle based on the projection image generated in step S17 in the same manner as in step S3 in this embodiment. That is, in step S17, the evaluation circle generation unit 17 specifies three cuspidal points from the projection image, and draws a straight line connecting the three cuspidal points on the projection image. With this operation, an evaluation circle is generated.

Note that an evaluation circle according to the second modification is generated based on the projection image of a sub-volume. However, the second modification is not limited to this. For example, it is possible to generate an evaluation circle based on a sectional image associated with a section set in a sub-volume. In this case, the evaluation circle generation unit 17 generates an evaluation circle based on a sectional image associated with a section set in a sub-volume in the same manner as in step S3 in this embodiment. An evaluation circle generated in step S18 will be referred to as a hetero-evaluation circle hereinafter.

Upon executing step S18, the control unit 29 causes the evaluation circle generation unit 17 to perform open/close index decision processing (step S19). In step S19, the evaluation circle generation unit 17 decides an open/close index according to the second modification for each of a plurality of pixels constituting a hetero-evaluation circle. An open/close index according to the second modification is decided in accordance with a pixel value. More specifically, when a pixel value originating from a blood flow is assigned to a processing target pixel, the evaluation circle generation unit 17 decides open/close index z=100%. In this case, the processing target pixel belongs to the valve cusp existing region. Note that a pixel value originating from a blood flow is a relatively high pixel value. In contrast, when a pixel value originating from the cardiac valve is assigned to a processing target pixel, the evaluation circle generation unit 17 decides open/close index z=0%. In this case, the processing target pixel belongs to the valve cusp non-existing region. A pixel value originating from the cardiac valve is a relatively low pixel value. The evaluation circle generation unit 17 generates an evaluation circle on which the cardiac valve region is superimposed, by assigning decided open/close indices to the pixels of the hetero-evaluation circle. This evaluation circle will be referred to as a valve-combined evaluation circle. The display unit 27 displays the generated valve-combined evaluation circle. In this case, the display unit 27 may display the cardiac valve region in the valve-combined evaluation circle in color corresponding to the open/close index or gray. In addition, the display unit 27 may display the ratio between the number of pixels of the valve cusp existing region included in the valve-combined evaluation circle and the number of pixels of the valve cusp non-existing region. This ratio may be displayed as a graph in the form of a color map.

Figure 23:
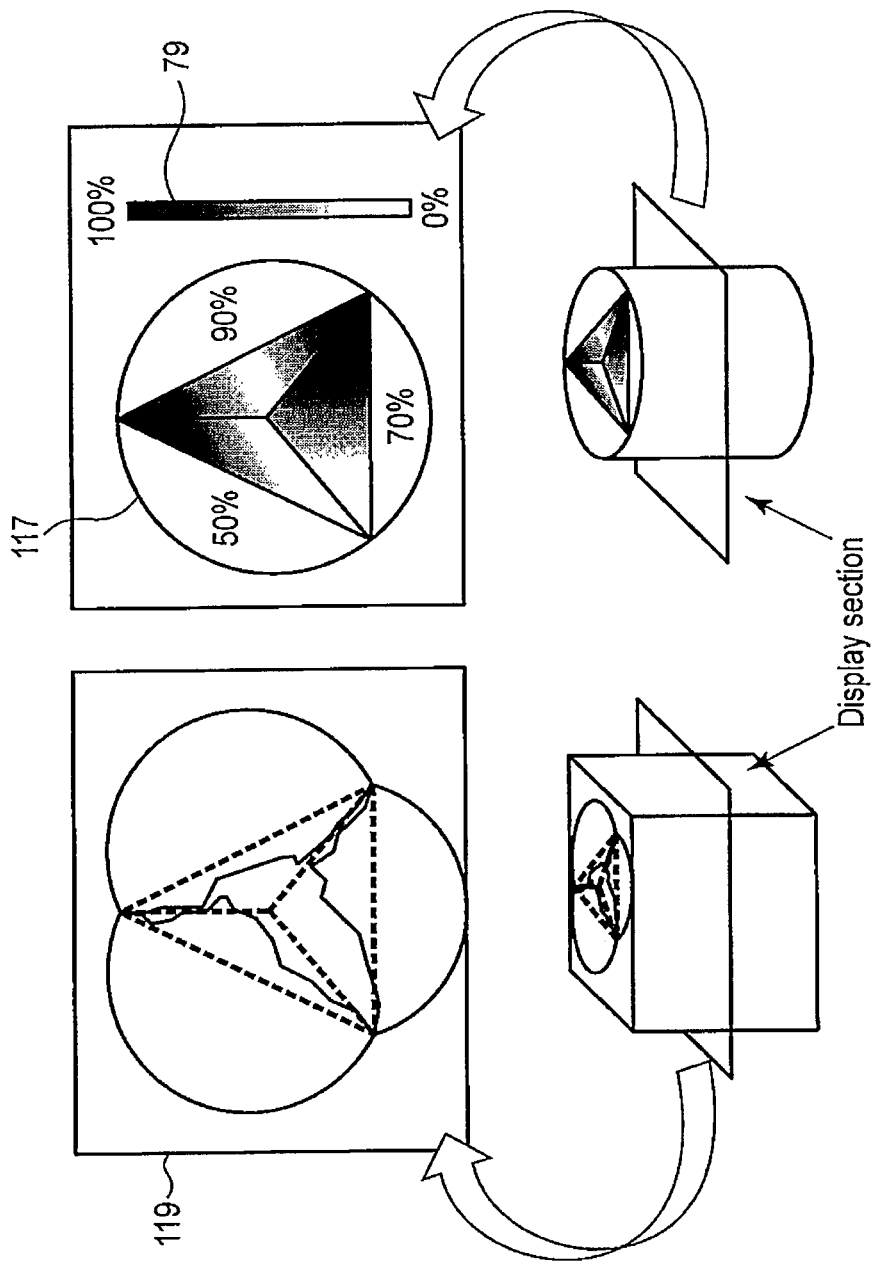
FIG. 23 is a view showing an example of display of a valve-combined evaluation circle generated in the second modification.

As described above, in some cases, a hetero-evaluation circle is generated based on an MPR image. FIG. 23 is a view showing a display example of a valve-combined evaluation circle when a hetero-evaluation circle 117 is generated based on an MPR image. As shown in FIG. 23, the display unit 27 preferably displays the MPR image and the valve-combined evaluation circle 117, which are associated with the same section, side by side. The user can arbitrarily set the position of a section via the operation unit 25. When the position of a section is changed, the display unit 27 links the position of the section of the MPR image with the position of the section of the valve-combined evaluation circle 117.

According to the second modification, the user need not set any evaluation section. Therefore, the image processing apparatus 1 according to the second modification can further improve the operation efficiency associated with a valvular disease by the user as compared with this embodiment.

(Third Modification)

In this embodiment, the cardiac valve is the aortic valve. Therefore, the number of valve cusps is three. However, the number of valve cusps in this embodiment is not limited to three, and can be changed in accordance with the type of cardiac valve, as needed. In addition, accordingly, the shape of a valve cusp can be changed from a triangle to another geometric shape such as a rectangle.

For example, the mitral valve has two valve cusps. FIGS. 24A, 24B, and 24C are views showing concrete examples of evaluation circles associated with the mitral valve. The evaluation circle in FIG. 24A depicts two valve cusps relatively similar to the actual shape of the mitral valve. The evaluation circle in FIG. 24B depicts two valve cusps having almost the same size and shape. The evaluation circle in FIG. 24B is simplified relative to the evaluation circle in FIG. 24A. The evaluation circle in FIG. 24C depicts two valve cusps having different sizes and shapes. The evaluation circle in FIG. 24C is more schematic than the evaluation circle in FIG. 24A, but depicts valve cusps more similar to the actual shape than the evaluation circle in FIG. 24B. The user can arbitrarily select one of the evaluation circles in FIGS. 24A, 24B, and 24C associated with the mitral valve according to his/her preference.

(Fourth Modification)

As shown in FIG. 25, the display unit 27 according to the fourth modification displays a combined image 121 of an MPR and a colored evaluation circle. The combined image 121 is, for example, an image obtained by superimposing a translucent colored evaluation circle on an MPR image. Displaying the combined image 121 allows the user to observe both the morphological information and open/close indices of the cardiac valve on one image.

In addition, various inventions can be formed by proper combinations of a plurality of constituent elements disclosed in the above embodiments. For example, several constituent elements may be omitted from all the constituent elements disclosed in the above embodiments. Furthermore, constituent elements in different embodiments may be properly combined.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising:
   a storage unit configured to store a three-dimensional image associated with a cardiac region of a subject;
   a specifying unit configured to specify a plurality of cardiac valves from a vascular region included in the three-dimensional image by image processing;
   a calculation unit configured to calculate index values indicating open/close degrees of the cardiac valves; and
   a display unit configured to display the index values;
   wherein the display unit displays a schematic valve image which schematically expresses shapes of the cardiac valves and also expresses the index values in different brightness or colors.

2. The image processing apparatus of claim 1, wherein the calculation unit calculates the index value for each of different portions of the heart for each of the cardiac valves.

3. The image processing apparatus of claim 1, further comprising a setting unit, an extraction unit, a first generation unit, a specifying unit, and a second generation unit,
   the setting unit setting a section in a vascular region included in the cardiac region,
   the extraction unit extracting a contour of the vascular region from the vascular region on the section by image processing,
   the first generation unit generating a schematic valve image schematically expressing a shape of a cardiac valve based on a shape of the contour,
   the specifying unit searching each pixel constituting the schematic valve image along a predetermined direction for a valve pixel associated with the cardiac valve included in the three-dimensional image and specifying whether the valve pixel exists, and
   the second generation unit generating a color image expressing an open/close degree of the cardiac valve for each pixel in color based on the schematic valve image and information indicating whether the valve pixel exists.

4. The image processing apparatus of claim 3, wherein the display unit displays the color image.

5. The image processing apparatus of claim 3, wherein the schematic valve image schematically expresses an estimated shape of a normal cardiac valve in an open state and an estimated shape of the normal cardiac valve in a closed state.

6. The image processing apparatus of claim 3, wherein the second generation unit assigns the each pixel color information corresponding to a degree of difference between an open/close degree associated with the cardiac valve of the subject and an open/close degree associated with the normal cardiac valve.

7. The image processing apparatus of claim 3, wherein the second generation unit generates the color image for a plurality of cardiac phases, and the display unit displays color images associated with the cardiac phases as a moving image.

8. The image processing apparatus of claim 3, wherein the extraction unit extracts a contour of a cardiac valve region from the cardiac valve region on an evaluation section by image processing, and
   the display unit displays the color image superimposed the contour of the cardiac valve region on.

9. An image processing apparatus comprising:
   a storage unit configured to store a three-dimensional image associated with a cardiac region of a subject;

a setting unit configured to set a section crossing a vascular region included in the cardiac region;
a first generation unit configured to generate a sectional image associated with the section based on the three-dimensional image;
a specifying unit configured to search the section along a predetermined direction for a valve pixel associated with a cardiac valve included in the three-dimensional image and specify the presence/absence of the valve pixel for each pixel constituting the sectional image; and
a second generation unit configured to generate a color image expressing the presence/absence of the valve pixel for each pixel in color based on the sectional image and the presence/absence of the valve pixel;
wherein the display unit displays a schematic valve image which schematically expresses shapes of the cardiac valve and also expresses degrees of opening/closing of the cardiac valve in different brightness or colors.

10. An image processing apparatus comprising:
a storage unit configured to store a three-dimensional image associated with a cardiac region of a subject;
a setting unit configured to set a section in a vascular region included in the cardiac region;
a specifying unit configured to specify a cardiac valve from the vascular region by image processing;
a generation unit configured to generate a schematic valve image schematically expressing a shape of the cardiac valve; and
a display unit configured to superimpose and display the cardiac valve on the schematic valve image upon alignment;
wherein the display unit displays a schematic valve image which schematically expresses shapes of the cardiac valve and also expresses degrees of opening/closing of the cardiac valve in different brightness or colors.

* * * * *

UNITED STATES PATENT AND TRADEMARK OFFICE
CERTIFICATE OF CORRECTION

PATENT NO. : 8,594,413 B2  
APPLICATION NO. : 13/343016  
DATED : November 26, 2013  
INVENTOR(S) : Yoshifumi Yamagata et al.

Page 1 of 1

It is certified that error appears in the above-identified patent and that said Letters Patent is hereby corrected as shown below:

On the title page, Item (60), the Related U.S. Application Data Information is incorrect.
Item (60), should read:

--Related U.S. Application Data

(60) Continuation of application No. PCT/JP2011/075330, filed on Nov. 2, 2011--

Signed and Sealed this
Eleventh Day of February, 2014

Michelle K. Lee
*Deputy Director of the United States Patent and Trademark Office*